| United States Patent [19] | [11] Patent Number: 4,778,886 |
|---|---|
| Borsdorff et al. | [45] Date of Patent: Oct. 18, 1988 |

[54] METHOD OF MANUFACTURING CIS-2,6-DIMETHYLMORPHOLINE

[75] Inventors: Horst-Wolfram Borsdorff, Oberhausen; Lothar Broschinski, Werl; Josef Disteldorf, Marl; Werner Huebel; Klaus Rindtorff, both of Recklinghausen, all of Fed. Rep. of Germany

[73] Assignee: Huls Aktiengesellschaft, Marl, Fed. Rep. of Germany

[21] Appl. No.: 152,473

[22] Filed: Feb. 5, 1988

[30] Foreign Application Priority Data

Mar. 19, 1987 [DE] Fed. Rep. of Germany ....... 3708931

[51] Int. Cl.$^4$ ......................................... C07D 265/28
[52] U.S. Cl. ................................................. 544/106
[58] Field of Search ......................................... 544/106

[56] References Cited

U.S. PATENT DOCUMENTS 3,083,202 3/1963 Summers .............................. 544/106
4,212,972 7/1980 Goetz et al. ........................ 544/106

OTHER PUBLICATIONS

Goetz, et al., *Chemical Abstracts*, vol. 102 (1985), No. 166763a.

*Primary Examiner*—Robert W. Ramsuer
*Attorney, Agent, or Firm*—Oblon, Fisher, Spivak, McClelland & Maier

[57] ABSTRACT

Cis-2,6-dimethylmorpholine is manufactured by catalytic isomerization of trans-2,6-dimethylmorpholine. A previously hydrogen-activated copper chromite catalyst is used for catalytic isomerization of the trans-2,6-dimethylmorpholine. The catalyst preferably also contains barium oxide and/or manganese dioxide. The process is carried out at 180°–300° C. and 1–500 bar absolute. The inexpensive novel catalyst enables conversions which are better than those with known methods.

5 Claims, No Drawings

METHOD OF MANUFACTURING CIS-2,6-DIMETHYLMORPHOLINE

BACKGROUND OF THE INVENTION

1. Field of the Invention

The invention relates to a method of manufacturing cis-2,6-dimethylmorpholine by isomerizing trans-2,6-dimethylmorpholine.

2. Discussion of Background

In the synthesis of dimethylmorpholine by the dehydration of diisopropanolamine in the presence of acid catalysts such as sulfuric acid (U.S. Pat. No. 3,083,202; Eur. Pat. 0 094 565; "Houben-Webyl", Vol. 6/4, pp. 510–520), mixtures of cis and trans isomers are always produced. Often it is the cis isomer which is preferred, for example, because of the higher effectiveness of plant protection agents or vulcanization accelerators produced from it (Ger. OS 26 57 747, OS 27 52 096, OS 27 52 135; U.S. Pat. No. 3,083,202). Accordingly, there is a demand for means of converting trans-2,6-dimethylmorpholine (formula I):

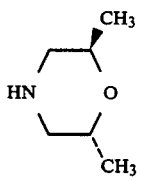

into cis-2,6-dimethylmorpholine (formula II):

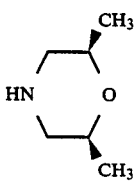

A number of means are known for increasing the content of the cis isomer in a cis/trans-2,6-dimethylmorpholine mixture. One such method is the isomerization of the mixture in an excess of concentrated or fuming sulfuric acid at 180°–220° C. (U.S. Pat. No. 3,083,202). Also, by appropriate control of the process, the cis-content can be increased at temperatures of only 150°–190° C.; however, this requires a substantial molar excess of sulfuric acid (Eur. Pat. 0 094 565).

Disadvantages of both of these methods include the necessary presence of alkali sulfates which are produced in the neutralization of the morpholine base, and yields which decrease (accompanied by increased by-product formation) with increasing degree of isomerization.

There are also various catalytic isomerization methods employing metallic hydrogenation catalysts in the presence of hydrogen which do not produce appreciable amounts of by-products and waste products. Thus, when one or more metals from group VIII or IB of the periodic table are employed, with temperatures of, in particular, 150°–250° C., in the most favorable cases isomerizations are attained which yield an isomer ratio (as given in Eur. Pat. 0 094 565) of 88:12 (cis/trans) after establishment of thermodynamic equilibrium.

According to the method of Eur. Pat. 0 007 520, Examples 7–8, conversions of 76.7 and 86.2%, with selectivities of 92.3 and 90.9%, respectively, were achieved after distillation, using a $Pd/Pr_2O_3$ catalyst, at temperatures of 230° and 250° C., respectively. Throughputs of 60 parts trans-2,6-dimethylmorpholine per hr and 10,000 vol parts hydrogen per hr were employed in a continuous flow system with 500 vol parts catalyst. Palladium showed superior effectiveness among the metals claimed.

Also, in Eur. Pat. 0 026 367, catalytic isomerization on metal catalysts comprised of Pd, Zn, Cd, and Mn is described, and in Eur. OS 0 129 904 the use of Pt, Ru, or Rh is described, wherein according to Example 1 of the former patent, with a catalyst comprising Pd, Zn and Cd, a conversion of 74.5% was achieved, with a selectivity of 94.6%, after distillation. According to Example 1a of the former patent, with a Pt catalyst, conversion 81.9% and selectivity 97.2% were achieved after distillation.

Here the throughput was 100 parts trans-2,6-dimethylmorpholine per hr, with 300,000 vol parts hydrogen per hr, over 1000 vol parts catalyst (0.1 parts trans-2,6-dimethylmorpholine with 100 vol parts hydrogen, over 1 vol part catalyst). The conversion and selectivity figures were calculated from the literature data, using the definitions in "Ullmanns Encyklopaedie der technischen Chemie", 4th Edition, Vol. 13, p. 550.

The isomerization catalysts according to Eur. Pats. 0 007 520 and 0 026 367 have the disadvantage of a rapid drop in activity because of the presence of sulfur compounds in technical 2,6-dimethylmorpholine. These sulfur compounds are inevitable impurities from the manufacturing process. The only exceptions are the last-mentioned noble metal catalysts based on Pt, Ru, or Rh. A further disadvantage of all three above-mentioned methods is the high price of the noble metal catalysts.

SUMMARY OF THE INVENTION

Accordingly, one object of the present invention is to devise a more economical method of isomerizing sulfur-containing trans-2,6-dimethylmorpholine, which also provides higher conversion.

This and other objects which will become apparent from the following specification have been achieved by the present invention in which trans-2,6-dimethylmorpholine is isomerized in the presence of hydrogen and a previously hydrogen-activated copper chromite catalyst at temperatures of 180°–300° C. and pressures of 1–500 bar absolute, particularly at temperatures of 220°–280° C. and pressures of 1–300 bar absolute.

DETAILED DESCRIPTION OF THE PREFERRED EMBODIMENTS

It is surprising that this inexpensive, easily obtainable type of catalyst is capable of better conversions than the above-mentioned noble metal catalysts. At times the selectivity of the isomerization reaction reaches nearly 100% with the present method. Good catalyst lifetimes can be experienced even with a sulfur-containing feed of trans-2,6-dimethylmorpholine containing on the order of 2–10 ppm by wt. sulfur.

The inventive method is carried out in the presence of hydrogen, and preferably in the gas phase. At relatively high pressures, however, the reaction is carried out in the liquid phase, which is either trickled or in the form of a liquid bath. Inert solvents may also be used, for example, alkanes, ethers, glycols, etc.

The catalyst is a copper chromite which preferably also contains barium oxide and/or manganese dioxide. Before being used for isomerization the catalyst must be activated by reductive treatment with hydrogen. In this treatment, care must be taken to avoid complete reduction to metallic copper. For the activation, the catalyst bed is heated to 130° C. under a stream of nitrogen, and then the nitrogen is replaced stepwise with hydrogen, taking care to limit the temperature of the catalyst bed to 160° C. The process is exothermic. The treatment brings about a partial reduction to univalent copper. At the same time, a corresponding amount of water of reaction is formed. It has been discovered that excess reduction of the catalyst will lead to a persistent degradation of the degree of isomerization.

In addition to CuO, $Cr_2O_3$, and preferably also BaO and/or $MnO_2$, the catalyst also contains an alkali binder which is necessary for forming. The BaO and/or $MnO_2$ serve to inhibit excess reduction. An oxidized copper chromite is used in industry as a hydrogenation catalyst, particularly with the mentioned stabilization; but if reduced to metallic copper, the catalyst changes to a dehydrogenation catalyst. Typical commercially available products comprising such BaO-doped copper chromite catalysts are, e.g., Mallinckrodt E 406 TU cored, and Harshaw Cu 1107 T 1/8 in, with CuO content varying from 42 to 33%.

The catalyst may be employed in any commonly used form which is suitable for producing a fixed bed, e.g., as tablets, pellets, rings, or extrudates. Also, the copper chromite may be employed on an inert support.

Other features of the invention will become apparent in the course of the following descriptions of exemplary embodiments which are given for illustration of the invention and are not intended to be limiting thereof.

EXAMPLES

In the Tables, the values of conversion and selectivity have been calculated uniformly in accordance with the definitions given in "Ullmanns Encyklopaedle der technischen Chemie", 4th Ed., Vol. 13, p. 550, namely:

Conversion U (%) = converted moles i/moles i fed $$\text{Selectivity } S\ (\%) = \frac{\text{moles of } i \text{ converted into } j}{\text{total moles of } i \text{ converted}}$$

EXAMPLE 1

500 ml of Mallinckrodt type E 406 TU cored catalyst, comprised of CuO (42 wt. %), $Cr_2O_3$ (40 wt. %), BaO (8 wt. %), and binder (10 wt. %), was charged to a 1 liter shaft kiln and heated to the desired temperature. The 2,6-dimethylmorpholine (DMM) employed (cis 5.7 wt. % and trans 91.9 wt. %), along with the hydrogen stream, was passed through the catalyst bed either in a trickling process with the liquid comprising 2,6-dimethylmorpholine for higher pressure systems, or in a gas phase process wherein the 2,6-dimethylmorpholine was vaporized on a packing layer disposed above the catalyst layer, for lower pressure systems.

The results are summarized in Table 1.

TABLE 1

| Run No. | Temp (°C.) | Process pressure (bar, absolute) | $H_2$—stream (liter/hr) | Feed of cis/trans-2,6-DMM (ml/hr) | reaction product GC*: 2,6-DMM (wt. %) | | Conversion (%) | Selectivity (%) |
|---|---|---|---|---|---|---|---|---|
| | | | | | cis- | trans- | | |
| 1 | 220 | 3 | 50 | 100 | 84.27 | 10.84 | 88.15 | 97.82 |
| 2 | 240 | 3 | 50 | 100 | 85.11 | 8.95 | 90.26 | 95.70 |
| 3 | 240 | 21 | 50 | 100 | 84.18 | 12.28 | 86.64 | 98.53 |
| 4 | 240 | 101 | 50 | 100 | 73.56 | 21.47 | 76.65 | 96.30 |
| 5 | 240 | 101 | 500 | 100 | 72.45 | 23.15 | 74.82 | 97.05 |
| 6 | 260 | 16 | 500 | 250 | 80.42 | 11.72 | 87.19 | 94.07 |
| 7 | 260 | 21 | 500 | 250 | 81.48 | 11.14 | 87.89 | 93.79 |
| 8 | 260 | 21 | 5,000 | 250 | 81.44 | 14.08 | 84.69 | 97.28 |
| 9 | 260 | 101 | 500 | 250 | 73.63 | 20.32 | 77.90 | 94.85 |
| 10 | 260 | 261 | 500 | 100 | 67.69 | 22.77 | 75.11 | 90.67 |

*Determined by gas chromotography

It is clear that the isomerization is better in the gas phase (pressure 3 bar absolute) than in the liquid phase (16, 21, 101, and 261 bar). If the hydrogen throughput is increased, the conversion decreases while the selectivity increases; however, the effect of increased hydrogen throughput on overall yield is minor.

There was no decrease in activity of the catalyst after more than 500 service hours.

EXAMPLE 2

The test procedure was as in Example 1, except that Harshaw type Cu 1107 T ⅛ in. catalyst was employed, comprised of CuO (33 wt. %), $Cr_2O_3$ (38 wt. %), BaO (9 wt. %), and binder (20 wt. %), and the feed comprised 7.0 wt. % cis-2,6-dimethylmorpholine and 88.0 wt. % trans-2,6-dimethylmorpholine.

The results are summarized in Table 2.

TABLE 2

| Run No. | Temp (°C.) | Process pressure (bar, absolute) | $H_2$—stream (liter/hr) | Feed of cis/trans-2,6-DMM (ml/hr) | reaction product GC: 2,6-DMM (wt. %) | | Conversion (%) | Selectivity (%) |
|---|---|---|---|---|---|---|---|---|
| | | | | | cis- | trans- | | |
| 1 | 240 | 1.25 | 50 | 150 | 73.5 | 17.0 | 80.7 | 93.7 |
| 2 | 240 | 3 | 50 | 150 | 79.1 | 11.7 | 86.7 | 94.5 |
| 3 | 240 | 4 | 50 | 150 | 80.7 | 11.1 | 87.4 | 95.8 |
| 4 | 240 | 6 | 50 | 150 | 78.4 | 14.3 | 83.8 | 96.9 |
| 5 | 240 | 11 | 50 | 150 | 77.7 | 15.4 | 82.5 | 97.4 |
| 6 | 240 | 21 | 50 | 150 | 72.6 | 21.2 | 75.9 | 98.2 |

Up to a pressure of 4 bar absolute, the conversion increases, while at higher pressures it decreases. The selectivity continues to increase with increasing pressure.

After more than 400 hr service time, no decrease in catalytic effectiveness was observable.

EXAMPLE 3

The test procedure was as in Example 1, except that a manganese dioxide doped catalyst, Harshaw type Cu 1932 T ⅛ in., was employed, comprised of CuO (35.7 wt. %), $Cr_2O_3$ (30.7 wt. %), $MnO_2$ (2.72 wt. %), and binder (30.88 wt. %), and the feed employed was 5.64 wt. % cis and 91.95 wt. % trans-2,6-dimethylmorpholine.

The results are given in Table 3.

TABLE 3

| Run No. | Temp (°C.) | Process pressure (bar, absolute) | $H_2$—stream (liter/hr) | Feed of cis/trans 2,6-DMM (ml/hr) | reaction product GC: 2,6-DMM (wt. %) cis- | trans- | Conversion (%) | Selectivity (%) |
| --- | --- | --- | --- | --- | --- | --- | --- | --- |
| 1 | 240 | 3 | 50 | 50 | 82.06 | 8.38 | 90.88 | 91.45 |
| 2 | 240 | 3 | 50 | 250 | 77.55 | 15.70 | 82.93 | 94.31 |
| 3 | 220 | 3 | 50 | 100 | 84.76 | 12.08 | 86.87 | 99.06 |

After more than 200 hr service time, no decrease in catalyst activity was observable.

EXAMPLE 4

The test procedure was as in Example 1, except that an un-stabilized copper chromite catalyst, Harshaw type Cu 1808 T ⅛ in., was employed, comprised of CuO (42.5 wt. %), $Cr_2O_3$ (38.75 wt. %), and binder (18.75 wt. %), and the feed employed was 5.64 wt. % cis and 91.95 wt. % trans-2,6-dimethylmorpholine (as in Example 3).

The results are given in Table 4.

TABLE 4

| Run No. | Temp (°C.) | Process pressure (bar, absolute) | $H_2$—stream (liter/hr) | Feed of cis/trans- 2,6-DMM (ml/hr) | reaction product GC: 2,6-DMM (wt. %) cis- | trans- | Conversion (%) | Selectivity (%) |
| --- | --- | --- | --- | --- | --- | --- | --- | --- |
| 1 | 240 | 3 | 50 | 100 | 71.71 | 25.65 | 72.10 | 99.65 |
| 2 | 260 | 3 | 50 | 100 | 74.59 | 19.85 | 78.41 | 95.62 |

This catalyst, containing neither of the dopants BaO or $MnO_2$, gave lower conversions than the catalysts in Examples 1–3.

EXAMPLE 5 (COMPARISON EXAMPLE)

The test procedure was as in Example 1, except that, for comparison, a copper-only catalyst, Harshaw type Cu 2501 G, was employed, comprised of Cu in the amount of 6 wt. % (as $CuCO_3$) on a silica support, and the feed employed was 5.64 wt. % cis and 91.95 wt. % trans-2,6-dimethylmorpholine (as in Example 3).

The results are given in Table 5.

TABLE 5

| Run No. | Temp (°C.) | Process pressure (bar, absolute) | $H_2$—stream (liter/hr) | Feed of cis/trans- 2,6-DMM (ml/hr) | reaction product GC: 2,6-DMM (wt. %) cis- | trans- | Conversion (%) | Selectivity (%) |
| --- | --- | --- | --- | --- | --- | --- | --- | --- |
| 1 | 240 | 3 | 50 | 100 | 34.80 | 61.33 | 33.3 | 95.2 |
| 2 | 260 | 3 | 50 | 100 | 30.84 | 67.92 | 29.7 | 91.7 |

It can be seen clearly that the conversions with this catalyst are far below those of the copper chromite catalyst.

EXAMPLE 6

A tubular reactor with 108 reactor tubes each 4 cm in diameter and 240 cm long was filled with 432.8 kg (325 liter) of a catalyst, Mallinckrodt type E 406 TU cored, comprised of CuO (42 wt. %), $Cr_2O_3$ (40 wt. %), BaO (8 wt. %), and binder (10 wt. %). A nitrogen stream of 30 m³/hr (at STP) was passed through, at the reaction temperature of 150° C. and atmospheric pressure, with gradual replacement of the nitrogen by hydrogen, the catalyst was activated, then the system was slowly brought to 2 bar gage pressure and 240° C.

After established of the desired reaction conditions, 115 liter/hr (107 kg/hr) 2,6-dimethylmorpholine was fed to an evaporator to be converted to gas phase, then was brought to the reaction temperature together with the preheated hydrogen stream in a superheater and was passed through the catalyst bed. The reaction mixture leaving the reactor was passed through a cooler-separator where it was separated into 2,6-dimethylmorpholine and hydrogen, and the excess hydrogen was recycled to the reactor.

The product 2,6-dimethylmorpholine was isomerized from the feed 2,6-dimethylmorpholine to a high degree, with good selectivity as well. After 720 service hours, there was no indication of loss of catalyst activity. The feed stream was 12.88% cis-2,6-dimethylmorpholine and 82.66% trans-2,6-dimethylmorpholine. The results for the product are given in Table 6.

TABLE 6

| Run No. | Temp (°C.) | Process pressure (bar, absolute) | $H_2$—stream (liter/hr) | Feed of cis/trans- 2,6-DMM (ml/hr) | reaction product GC: 2,6-DMM (wt. %) cis- | trans- | Conversion (%) | Selectivity (%) |
| --- | --- | --- | --- | --- | --- | --- | --- | --- |
| 1 | 240 | 3 | 40 | 115 | 84.90 | 7.36 | 91.1 | 95.6 |

TABLE 6-continued

| Run No. | Temp (°C.) | Process pressure (bar, absolute) | H$_2$—stream (liter/hr) | Feed of cis/trans-2,6-DMM (ml/hr) | reaction product GC: 2,6-DMM (wt. %) | | Conversion (%) | Selectivity (%) |
| --- | --- | --- | --- | --- | --- | --- | --- | --- |
| | | | | | cis- | trans- | | |
| 2 | 240 | 3 | 30 | 115 | 84.24 | 7.61 | 90.8 | 95.0 |
| 3 | 240 | 3 | 20 | 115 | 84.21 | 7.11 | 91.4 | 94.4 |

These results demonstrate that one can achieve good conversion and selectivity while at the same time having high catalyst loads and long catalyst life.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States:

1. A method of manufacturing cis-2,6-dimethylmorpholine by isomerizing trans-2,6-dimethylmorpholine, comprising the steps of:
   contacting trans-2-6-dimethylmorpholine with a hydrogen-activated copper chromite catalyst; and
   isomerizing said trans-2,6-dimethylmorpholine in the presence of hydrogen gas and said hydrogen-activated copper chromite catalyst at temperatures of 180°-300° C. and pressures of 1-500 bar absolute.

2. The method of claim 1, wherein said isomerizing step is carried out in the presence of a copper chromite catalyst which additionally comprises barium oxide, manganese dioxide or mixtures thereof.

3. The method of claim 1, wherein said isomerizing step is carried out at temperatures of 220°-280° C.

4. The method of claim 1, wherein said isomerizing step is carried out at pressures of 1-300 bar absolute.

5. The method of claim 1, wherein said trans-2,6-dimethylmorpholine further comprises cis-2,6-dimethylmorpholine.

* * * * *